(12) United States Patent
Rezach et al.

(10) Patent No.: US 7,578,822 B2
(45) Date of Patent: Aug. 25, 2009

(54) INSTRUMENT FOR COMPRESSION OR DISTRACTION

(75) Inventors: Alan Rezach, Atoka, TN (US); Douglas N. Baker, Collierville, TN (US); Greg Denzer, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 508 days.

(21) Appl. No.: 11/118,641

(22) Filed: Apr. 29, 2005

(65) Prior Publication Data

US 2006/0247649 A1 Nov. 2, 2006

(51) Int. Cl.
*A61B 17/60* (2006.01)

(52) U.S. Cl. .......................................... 606/90; 606/57

(58) Field of Classification Search ...................... 60/61, 60/86, 90; 606/57, 104, 61, 86, 90
See application file for complete search history.

(56) References Cited

U.S. PATENT DOCUMENTS

| | | | | |
|---|---|---|---|---|
| 2,391,537 A * | 12/1945 | Anderson | ...................... | 606/59 |
| 4,386,603 A * | 6/1983 | Mayfield | ..................... | 606/105 |
| 4,733,657 A | 3/1988 | Kluger et al. | | |
| 4,848,368 A * | 7/1989 | Kronner | ....................... | 606/57 |
| 4,957,495 A * | 9/1990 | Kluger | ......................... | 606/58 |
| 5,053,034 A * | 10/1991 | Olerud | ........................ | 606/246 |
| 5,478,340 A | 12/1995 | Kluger et al. | | |
| 5,890,271 A * | 4/1999 | Bromley et al. | ............... | 29/263 |
| 2002/0193802 A1* | 12/2002 | Zdeblick et al. | ............... | 606/96 |
| 2003/0149341 A1 | 8/2003 | Clifton | | |
| 2003/0167059 A1* | 9/2003 | Young | ........................... | 606/61 |
| 2004/0204710 A1* | 10/2004 | Patel et al. | .................... | 606/53 |
| 2005/0203532 A1* | 9/2005 | Ferguson et al. | .............. | 606/90 |

FOREIGN PATENT DOCUMENTS

| FR | 2 821 543 | 9/2002 |
|---|---|---|
| WO | WO 90/02527 A | 3/1990 |

* cited by examiner

*Primary Examiner*—Eduardo C Robert
*Assistant Examiner*—Elana B Fisher

(57) ABSTRACT

An apparatus for use in orthopedic distraction or compression is disclosed. In the illustrated embodiments, two arms are provided that are connected by a rod or bar with a mechanism that enables the arms to be brought toward or away from each other. At the end of each arm, an assembly for connecting to a bone implant is provided. The assemblies are pivotable with respect to the arms, and allow some rotational motion between parts of the assembly so as to accommodate different positions of the bone implants. Once the assemblies are appropriately positioned, connected and locked to the bone implants, the mechanism can be operated to move the arms together in compression or apart in distraction.

35 Claims, 15 Drawing Sheets

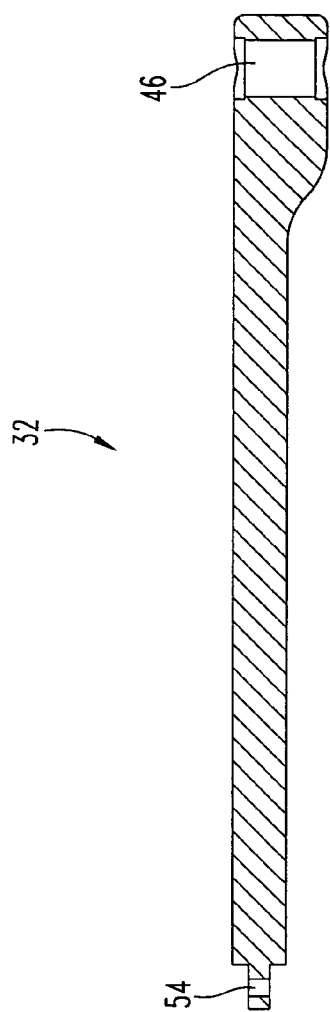
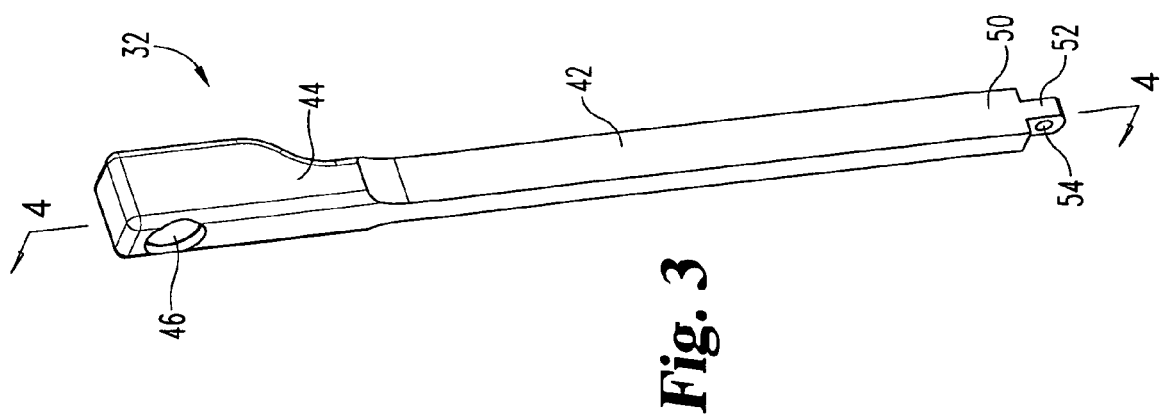
Fig. 4
Fig. 3

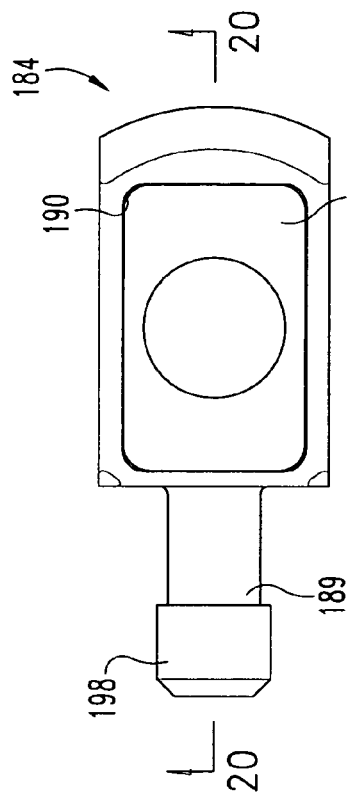
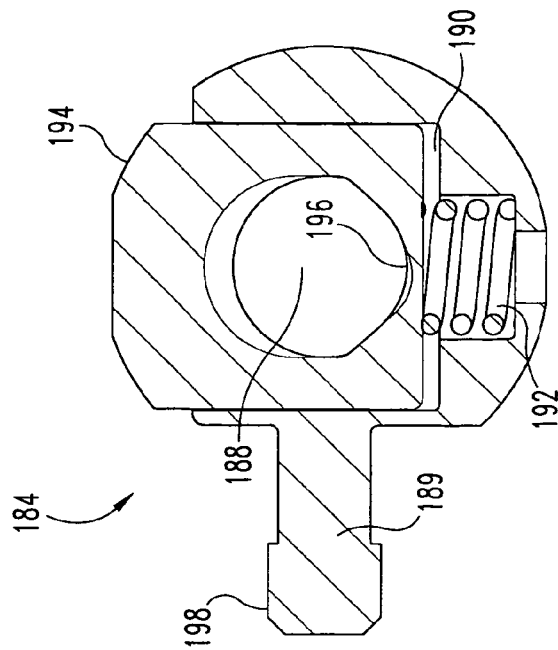
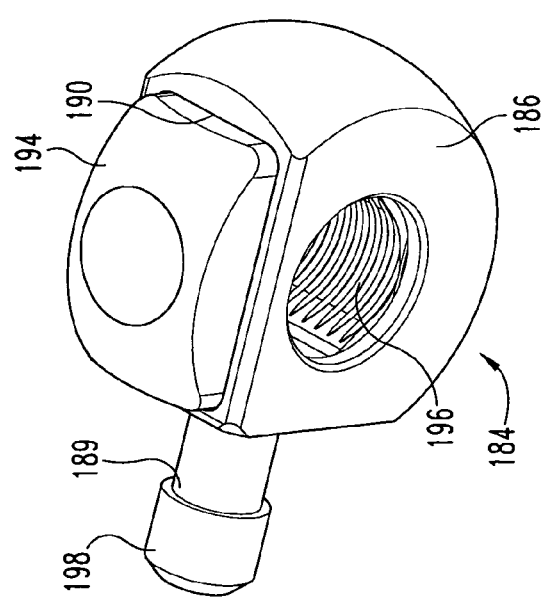
Fig. 19
Fig. 20
Fig. 18

INSTRUMENT FOR COMPRESSION OR DISTRACTION

The present disclosure relates to instrumentation useful in orthopedic surgery, and in particular to instrumentation useful in compressing (moving together) or distracting (moving apart) tissues such as bones (e.g. vertebrae) or bone fragments.

BACKGROUND

Several types of tools for compressing or distracting tissues such as bones or bone fragments toward healing of a trauma or correcting of an abnormality are known. Among these include instruments that use cables to pull together bones or artificial implants placed in such bones, scissor-like tools that apply leverage around a central fulcrum to move bones or implants toward or away from each other, and even the surgeon's own hands. Such manipulations or adjustments of bones are indicated for correction of a number of orthopedic conditions. For example, in the case of a scoliosis or other abnormal positioning of the spine, one or more vertebrae or vertebral segments may require compression or distraction with respect to adjacent bones to achieve a better or more normal position. In the case of a trauma, for example after an injury to a bone or adjacent tissue or removal of a cancerous or other mass, compression or distraction of tissue may be required to induce proper healing, to accommodate a therapy such as implantation of spacing or holding devices or of therapeutic material (e.g. bone morphogenic protein (BMP), allograft, autograft or other osteogenic substances, or medications), or for other reasons. Prior compression and/or distraction tools are not always useful, or may be awkward to use, in certain surgical pathologies or situations. Thus, there remains a need in the art for such instruments that provide advantages over existing tools.

BRIEF DESCRIPTION OF THE DRAWINGS

FIG. 3 is a perspective view of an embodiment of an aspect of the embodiment shown in FIG. 1.

FIG. 4 is a cross-sectional view of the structure shown in FIG. 3, taken along the lines 4-4 in FIG. 3 and viewed in the direction of the arrows.

FIG. 18 is a perspective view of an aspect of the embodiment shown in FIG. 17.

FIG. 19 is a top view of the structure shown in FIG. 18.

FIG. 20 is a cross-sectional view of the structure shown in FIG. 18, taken along the lines 20-20 in FIG. 19 and viewed in the direction of the arrows.

DESCRIPTION OF THE ILLUSTRATED EMBODIMENTS

Figure 1:
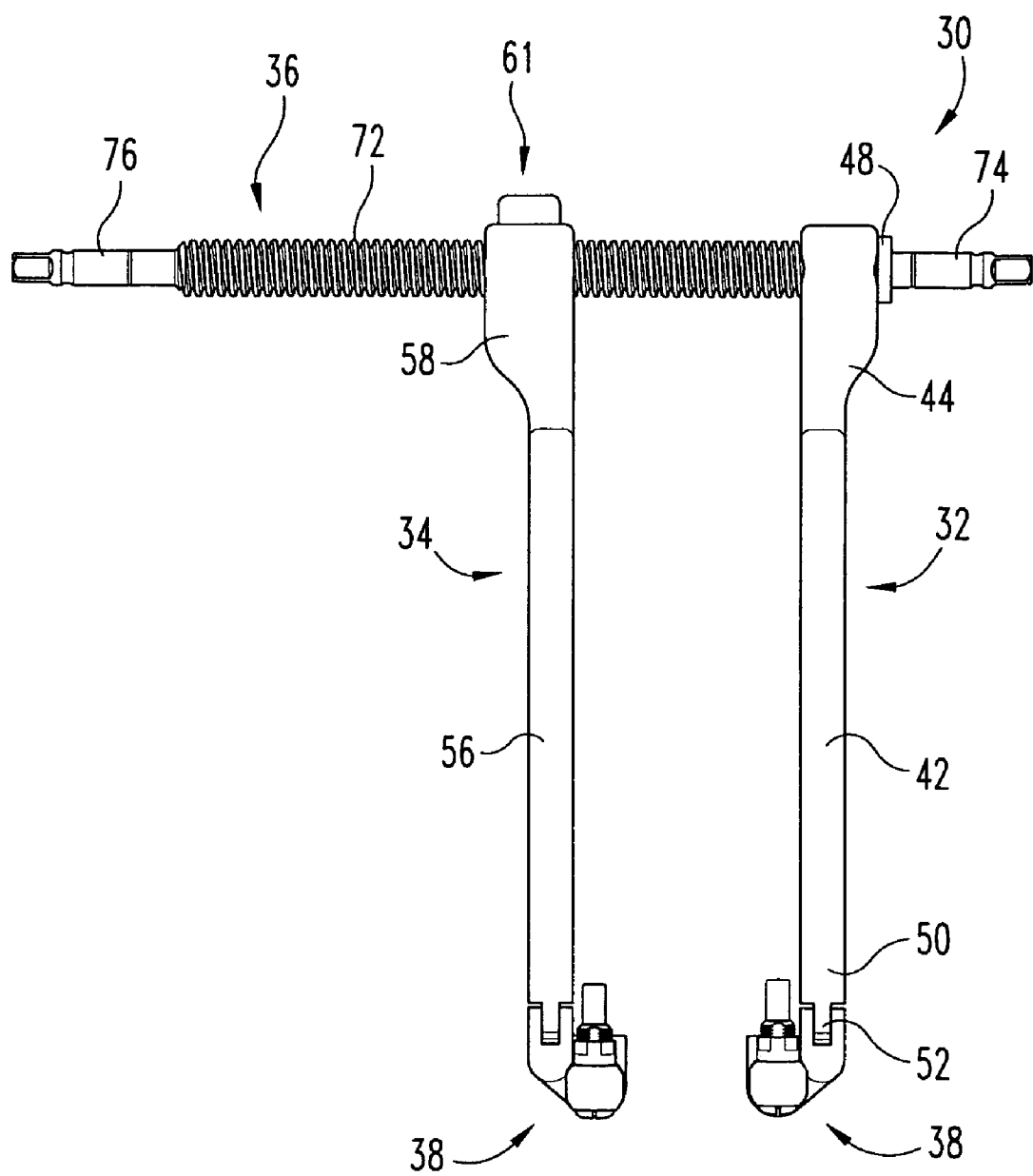
FIG. 1 is a front view of an embodiment of an instrument useful in orthopedic surgery.
Figure 2:
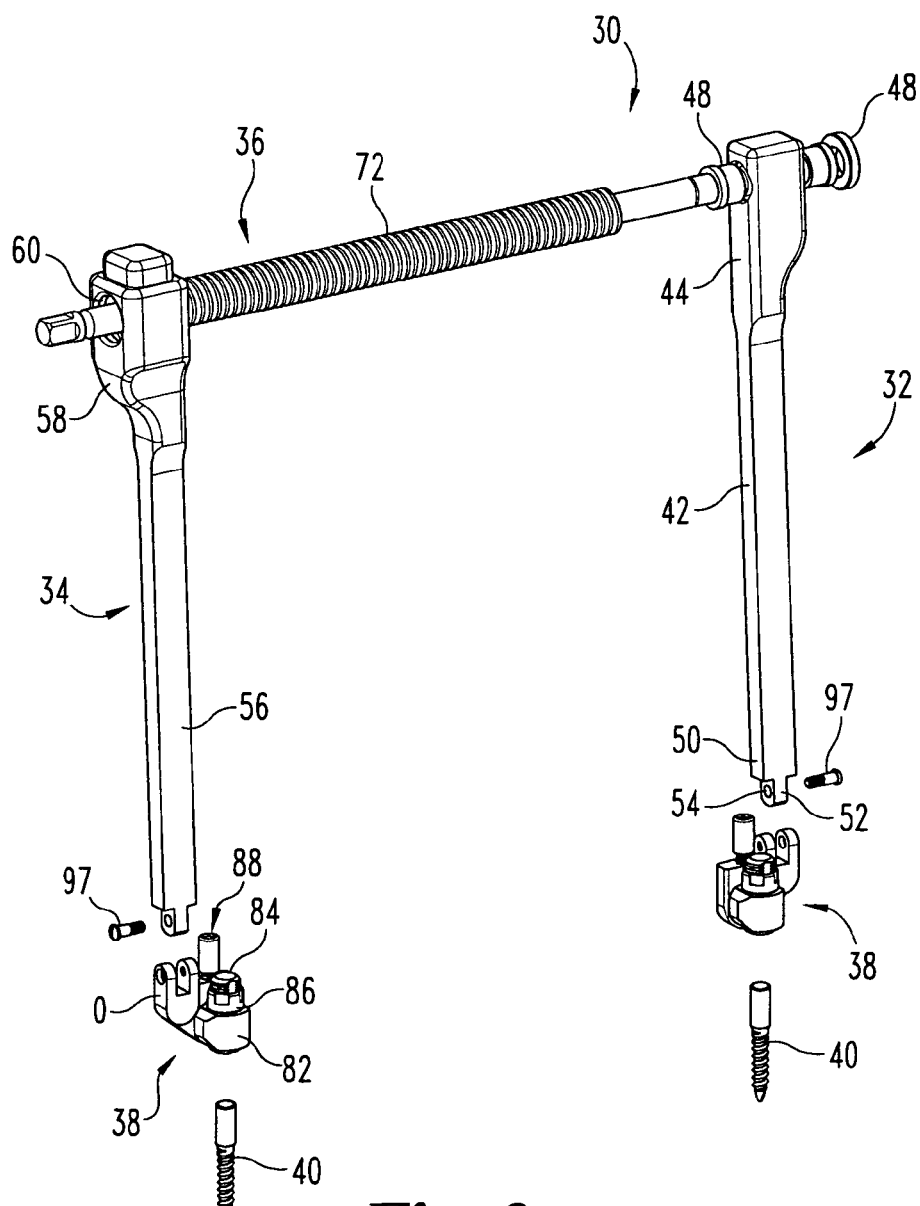
FIG. 2 is a partial exploded view in perspective of the embodiment shown in FIG. 1.
Figure 7:
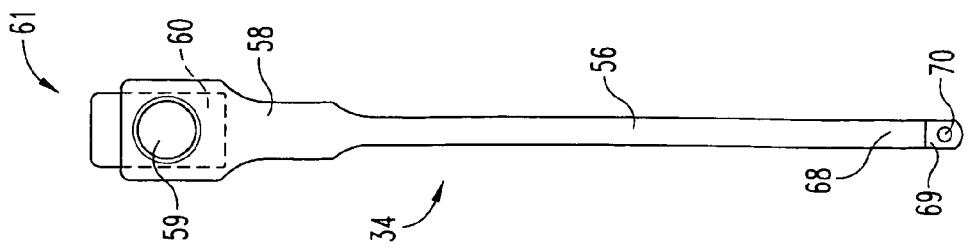
FIG. 7 is a side view of the structure shown in FIG. 5.
Figure 6:
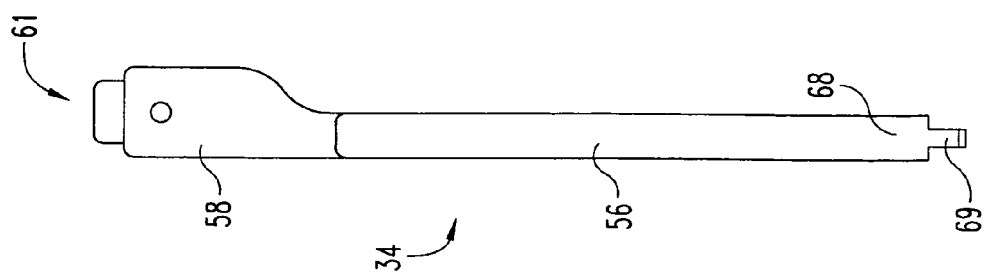
FIG. 6 is a rear view of the structure shown in FIG. 5.
Figure 5:
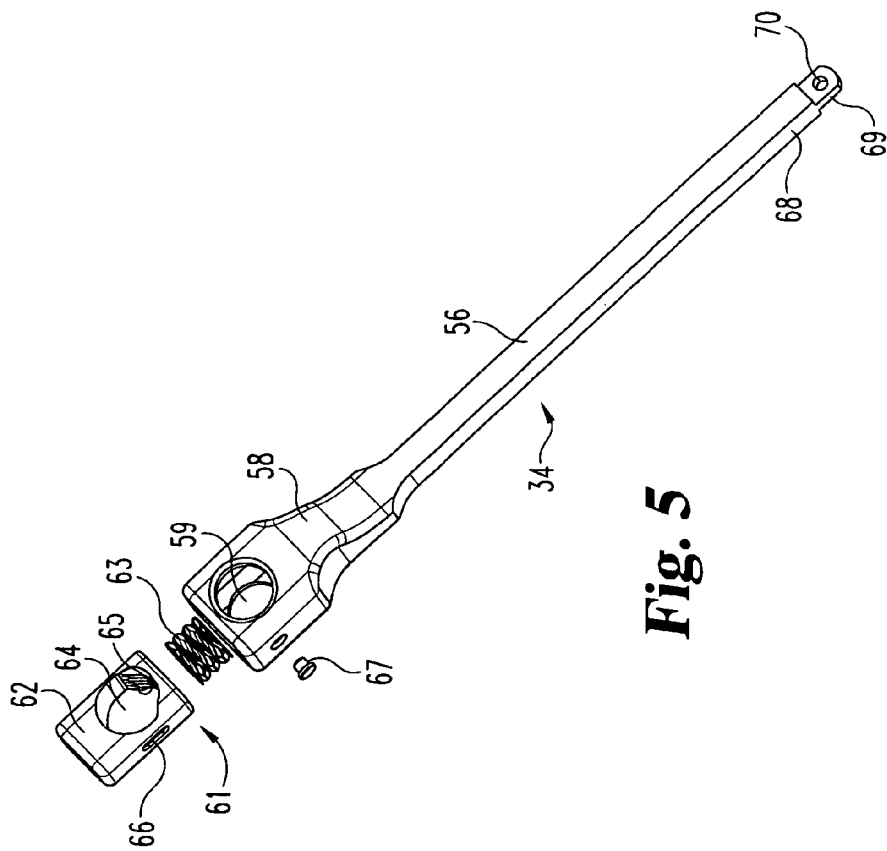
FIG. 5 is an exploded view in perspective of an embodiment of another aspect of the embodiment shown in FIG. 1.
Figure 8:
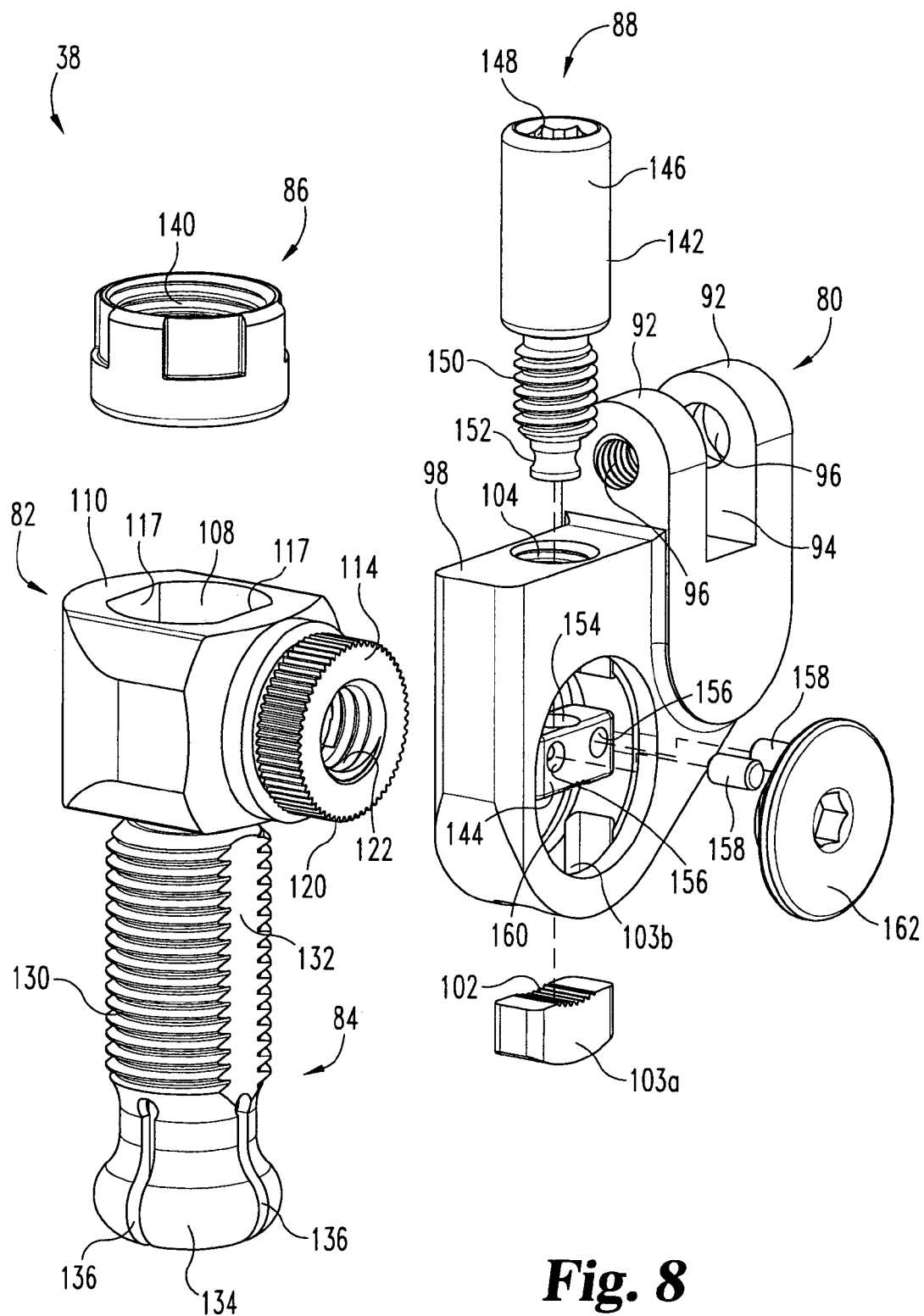
FIG. 8 is an exploded view in perspective of an embodiment of another aspect of the embodiment shown in FIG. 1.
Figure 10:
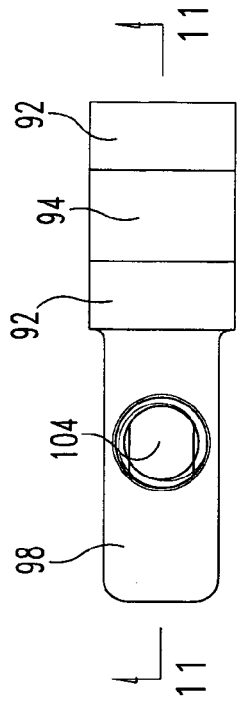
FIG. 10 is a top view of the structure shown in FIG. 9.
Figure 11:
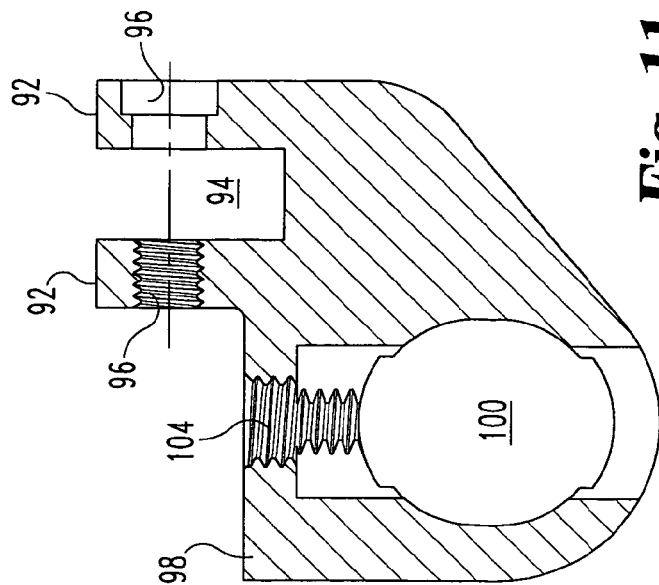
FIG. 11 is a cross-sectional view of the structure shown in FIG. 8, taken along the lines 11-11 in FIG. 9 and viewed in the direction of the arrows.
Figure 9:
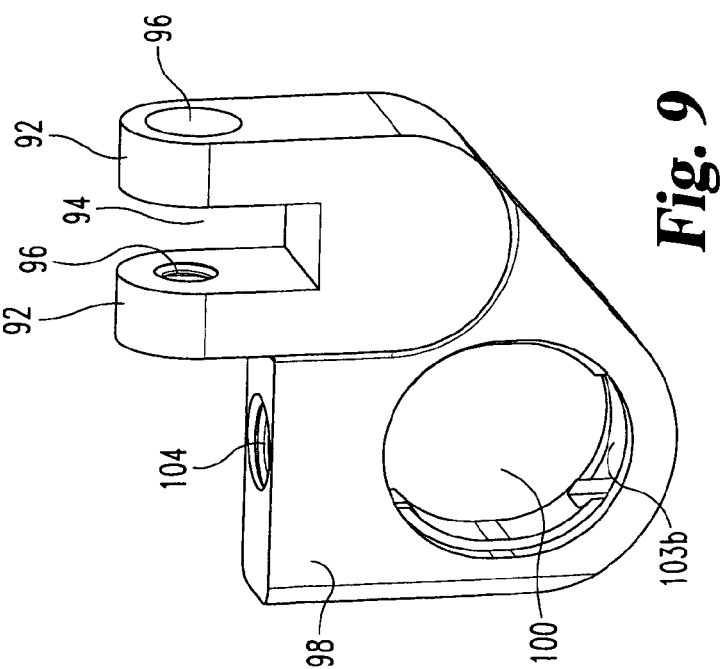
FIG. 9 is a perspective view of a part of the structure shown in FIG. 8.
Figure 14:
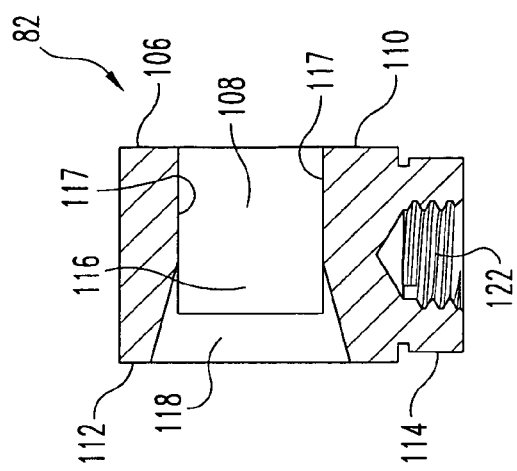
FIG. 14 is a cross-sectional view of the structure shown in FIG. 12, taken along the lines 14-14 in FIG. 13 and viewed in the direction of the arrows.
Figure 13:
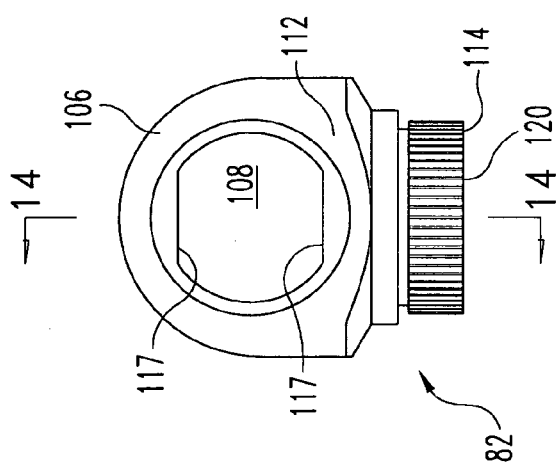
FIG. 13 is a bottom view of the structure shown in FIG. 12.
Figure 12:
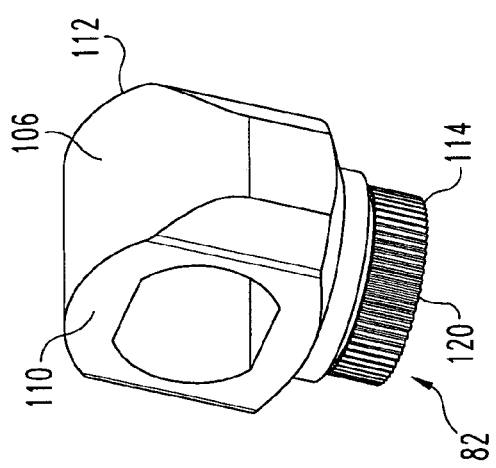
FIG. 12 is a perspective view of another part of the structure shown in FIG. 8.
Figure 15:
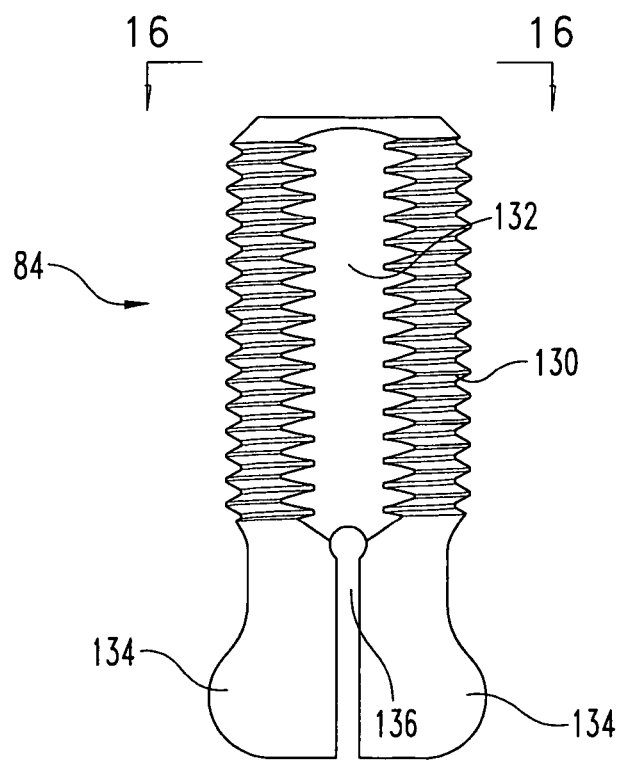
FIG. 15 is a side view of another part of the structure shown in FIG. 8.
Figure 16:
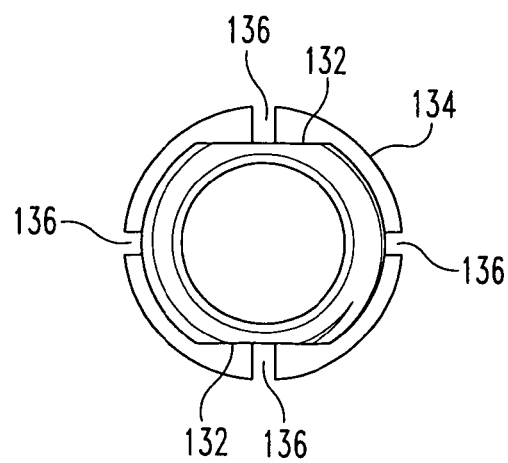
FIG. 16 is a top view of the structure shown in FIG. 15.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated, as would normally occur to one skilled in the art to which the invention relates.

An embodiment of an instrument 30 is shown in FIG. 1. In that embodiment, instrument 30 includes a first elongated arm 32, a second elongated arm 34, and a threaded rod 36 connected to arms 32 and 34. In a particular embodiment, arm 32 is fixed with respect to rod 36, and arm 34 is movable with respect to rod 36. In an alternative embodiment, arm 34 could be fixed with respect to rod 36, and arm 32 could be movable with respect to rod 36. At an end of arm 32 opposite from rod 36, there is an assembly 38 for connecting to an orthopedic implant 40. Such implants may include bone hooks or screws, and in one embodiment may be a Schanz-type screw with a relatively smooth, cylindrical upper portion. Other types of implants could also be used with the illustrated embodiment of instrument 30. A similar assembly 38 is positioned at the end of arm 34 opposite rod 36.

Arm 32 has a medial portion 42 that in the depicted embodiment has a substantially square or rectangular cross-section. Medial portion 42 may also be substantially cylindrical or of other appropriate shape in cross-section. At a first end 44 of arm 32, a hole 46 is provided to accommodate rod 36. Hole 46 is substantially smooth in the illustrated embodiment. Bushings or washers 48 are provided that fit around rod 36 and may extend at least partially into hole 46 to allow rod 36 to rotate with respect to arm 32, while limiting or inhibiting substantial movement of arm 32 along rod 36. Such bushings, if provided, may be tightly fitted, welded or otherwise attached to rod 36. Arm 32 may move between bushings 48 if the distance between bushings 48 is greater than the width of end 44. Other embodiments may include other mechanisms, such as pins or balls provided through end 44 that at least partially intersect hole 46, which are designed to engage rod 36 or grooves or indentations in it. End 44, in the illustrated embodiment, has a somewhat larger cross-section than medial portion 42. A second end 50 of arm 32 includes a tongue 52 with a hole 54 for accommodating an axle.

Arm 34 is substantially similar, in the illustrated embodiment, to arm 32. A medial portion 56 is provided that is substantially the same as or identical to medial portion 42 of arm 32. A first end portion 58 has a hole 59 and an aperture 60 through its top, and may be of somewhat larger cross-section than medial portion 56. A release mechanism 61 is provided at end 58. The illustrated embodiment of release mechanism 61 includes a button 62 and a spring 63. Button 62 includes an opening 64 with a threaded bottom 65, which is compatible with threads on rod 36, and a side slot 66. Spring 63 fits within end 58, and button 62 sits atop spring 63 so that rod 36 can extend through hole 59 and opening 64, and so that the top of button 62 is above the top of end 58. A pin 67 fits through end 58 and into slot 66 to keep spring 63 from ejecting button 62 from end 58. Pressing button 62 allows a threaded portion of rod 36 to be pulled through hole 59 without turning rod 36. Releasing button 62 when a threaded portion of rod 36 is in opening 64 results in the threaded engagement of bottom 65 of button 62 with rod 36. As with the illustrated embodiment of arm 32, arm 34 has a second end 68, with a tongue 69 having a hole 70 for an axle.

Rod 36 includes a threaded portion 72 and unthreaded end portions 74 and 76, in the illustrated embodiment. Part or all of ends 74 and/or 76 may have substantially square cross-sections, and a knob (not shown) may be integral with or fitted onto either end (e.g. end 74). Turning rod 36 in one direction moves arm 34 away from arm 32, and turning rod 36 in the other direction moves arm 34 toward arm 32. In embodiments in which one or both ends 74 and 76 have a square cross-section, rod 36 may be turned by a tool such as a nut driver or wrench with a square imprint or slot, or by a gripping tool such as a pliers. In embodiments having a knob, rod 36 may be turned by turning the knob.

One assembly 38 connects to arm 32 and another assembly 38 connects to arm 34, in the illustrated embodiment. Each assembly 38 connects to a respective implant that have each been implanted in bone tissue, for example a vertebra. For convenience, assembly 38 will be described below with reference to arm 32. It will be understood that the illustrated embodiment of assembly 38 operates with arm 34 in substantially the same way. Assembly 38 includes a connecting body 80 that connects to arm 32, an extension 82 that connects to the connecting body 80, a collet 84 that substantially surrounds a portion of an implant and fits at least partially within extension 82, a nut 86 that connects to an upper portion of collet 84, and a locking assembly 88.

Connecting body 80 in the illustrated embodiment is a relatively flat piece having a pair of prongs 92 defining a slot 94. Each of prongs 92 includes a hole 96, one of which may be threaded. Slot 94 is sized and configured to be able to mate with tongue 50 of arm 32. For example, tongue 50 may fit into slot 94 so that hole 54 through tongue 50 substantially aligns with holes 96 through prongs 92. An axle 97, which may be a partially threaded screw when one of holes 96 is threaded, is passed through holes 96 and hole 54, linking arm 32 and connecting body 80 so that they can rotate with respect to each other. A similar connection can be made between a connecting body 80 and arm 34.

Connecting body 80 also includes, in the illustrated embodiment, a side portion 98 through which a hole 100 extends. Hole 100 is generally oval-shaped in one embodiment, and is sized and configured to accommodate part of extension 82, as further discussed below. A set of splines 102 may be formed or placed along a bottom portion of hole 100, or otherwise positioned within hole 100. In a particular embodiment, splines 102 are on a block 103a that is fixed (e.g. by welding or other fixing method) in an opening 103b in the bottom of body 80. An opening 104 is provided for part of locking assembly 88, as will be further discussed below. In the illustrated embodiment, opening 104 is threaded for a set screw.

Extension 82 includes a holding portion 106 having a hole 108 from a top surface 110 to a bottom surface 112, and a leg portion 114 generally laterally offset from holding portion 106. Hole 108 has a portion 116 that is part cylindrical with flat walls 117, and a generally conical portion 118. Portions 116 and 118 could be otherwise configured, e.g. including concave or convex surfaces. Hole 108 is generally sized to accommodate collet 84 as further described below. Leg portion 114 is generally cylindrical in the illustrated embodiment, but may be oval, square, or otherwise configured in cross-section. Leg 114 has an outer surface that includes a series of splines 120 that are preferably substantially parallel to a longitudinal axis of portion 114. In one embodiment, splines 120 extend substantially around the entire diameter of leg 114, and extend along substantially the entire length of leg 114. It will be seen that only certain parts, such as a relatively upper and relatively lower part of leg 114, may include splines 120. Leg 114 may have an opening, such as threaded opening 122 in the illustrated embodiment, or may be solid or partially or completely filled.

Collet 84 includes a substantially cylindrical internal hole 124 from a top surface 126 to a bottom area 128. Externally, the illustrated embodiment of collet 84 includes a threaded portion 130 with flat portions 132 on one or more sides of collet 84. A lower portion of collet 84 includes a convex portion 134, which may be spherically convex, and a series of slots 136. The distance between flat portions 132 is slightly less than the distance between flat walls 117 in extension 82, in one embodiment. Collet 84 is inserted within hole 108 of extension 82. Hole 124 through collet 84 is sized and configured to accommodate part of an implant.

Nut 86 is provided with internal threads 140 that correspond to threaded portion 130 of collet 84. As will be further described below, nut 86 threads onto threaded portion 130 of collet 84 and against top surface 110 of extension 82, to pull collet 84 along hole 108 of extension 82.

Locking assembly 88 includes a set screw 142 and a block 144 connected to set screw 142. Set screw 142, in the illustrated embodiment, has a head portion 146 that is substantially smooth and cylindrical and includes an internal print 148 in a top portion, and a threaded portion 150 that includes a substantially circular or annular groove 152. Block 144 includes a hole 154 to accommodate the threaded portion 150 of set screw 142, and two smaller holes 156 that communicate with hole 154. Pins 158 are inserted through holes 156 so that they are at least partially in groove 152 when set screw 142 is inserted into block 144. Pins 158 may be of substantially the same diameter as holes 156 and groove 152. Splines 160 are on an underside of block 144, in one embodiment, to interact with splines 120 on leg 114. A cap 162 may be fitted into opening 122 in extension 82 to hold extension 82 and body 80 together.

Assembly 38 is assembled substantially as noted above, with collet 84 within hole 108 of extension 82, leg 114 of extension 82 inserted into hole 100 of connecting body 80, and locking assembly 88 in connecting body 80. Nut 86 may be loosely threaded around threaded portion 130 of collet 84, or may be initially separate and attached to collet 84 later. Separate assemblies 38 are connected to arms 32 and 34 by inserting tongues 50 and 66 into slot 94 of the respective connecting bodies 80, and connecting them together via a screw 97 or other axle. At this point, each assembly 38 is pivotable relative to its respective arm 32 or 34, and extension 82 is rotatable with respect to connecting body 80 around the longitudinal axis of leg 114 of extension 82. Such rotation of extension 82 with respect to body 80 may be substantially in a sagittal plane when instrument 30 is used in spinal surgery, depending on the location and/or orientation of the implants to which instrument 30 is connected.

Use of the illustrated embodiment of instrument 30 will now be described with reference to a surgical procedure on the spine using bone screws, as an example. As noted above, instrument 30 may be used in a variety of orthopedic treatments, at other surgical sites, and/or with other types of implants.

To treat the condition or injury of the patient, the surgeon obtains access to the surgical site in a manner well known in the art, e.g. through incision and retraction of tissues. Once access to the surgical site has been obtained, e.g. via an opening such as a midline incision above the affected area, with tissue being resected laterally to the transverse process, or by other surgical procedure. The surgeon may connect one or more implants to adjacent or nearby vertebrae that require compression or distraction in order to relieve or improve their condition. For example, pilot holes in vertebrae, e.g. in pedicles, may be made, and screws may be inserted into or otherwise connected to two or more vertebrae. In one embodiment, a support member (for example, a spinal rod, with or without appropriate lateral or other connectors) may be connected to the implants, and tightened to one of the implants.

Once such implants are placed as desired by the surgeon, the surgeon can move instrument 30 into position adjacent the implants. The surgeon may first adjust the distance between arms 32 and 34 to approximately the distance between the inserted bone screws, by turning threaded rod 36 and/or by using release mechanism 61. With arms 32 and 34 adjusted with respect to each other so that their respective assemblies 38 are adjacent the inserted implants, each implant is inserted through a respective collet 84 of adjacent assembly 38. Each implant may be inserted into a respective collet 84 to any of a number of depths. For example, one can be inserted into a collet 84 so that a top portion extends above top surface 126 of collet 84, while another may be inserted into another collet 84 so that the top extends half-way or slightly more through the hole 124 of that collet 84. This ability for variable height adjustment makes it easier for the surgeon to connect instrument 30 to a pair of screws, the tops of which may not be substantially even in height. Further, extension 82 can be rotated with respect to connecting body 80 as noted above, and thus the surgeon may rotate extension 82 so that collet 84 is substantially collinear with a bone screw.

Once the screws are within their respective collets 84 as the surgeon desires, nut 86 is tightened on threaded portion 130 of collet 84. Tightening nut 86 against upper surface 110 of extension 82 draws collet 84 along hole 108, and forces convex surfaces 134 against the inner surface of hole 108. Thus, tightening nut 86 forces compression of the lower portion 134 and slots 136 of collet 84, squeezing lower portion 134 against the implant to lock collet 84 and the implant together.

To tighten extension 82 with respect to connecting body 80, set screw 142 is tightened with respect to connecting body 80. Tightening set screw 142 with respect to connecting body 80 forces block 144 downward and into contact with leg 114 of extension 82. Splines 160 on the underside of block 144 engage splines 120 on the surface of leg 114 of extension 82. As set screw is further tightened, a lower portion of leg 114 will engage a bottom portion of hole 100 in connecting body 80, and in the embodiment in which hole 100 includes splines 102 on a bottom part, splines 120 on leg 114 will engage such splines 102. Thus, by tightening set screw 142, rotation of extension 82 with respect to connecting body 80 is inhibited, and extension 82 is held with respect to connecting body 80 at a desired angular position. If implants are locked to assemblies 38 first, then rotational adjustments to the implanted vertebra(e) can be made by rotating extension 82 with respect to connecting body 80. Locking extension 82 with respect to body 80 retains such vertebra(e) in the adjusted position.

Once the bone screws are connected to their respective assemblies 38, compression or distraction of the bones to which the bone screws are attached can occur. The surgeon may turn rod 36 in one direction to bring arm 34 toward arm 32, to achieve compression of the bones. Conversely, the surgeon may turn rod 36 in the other direction to move arm 34 away from arm 32, resulting in distraction of the bones. Once distraction or compression is performed to the surgeon's satisfaction, a support member may be tightened to one or both of the implants to maintain the distracted or compressed state of the vertebrae. Instrument 30 may be removed by loosening nuts 86 on assemblies 38 and sliding collets 84 off their respective implants.

Figure 17:
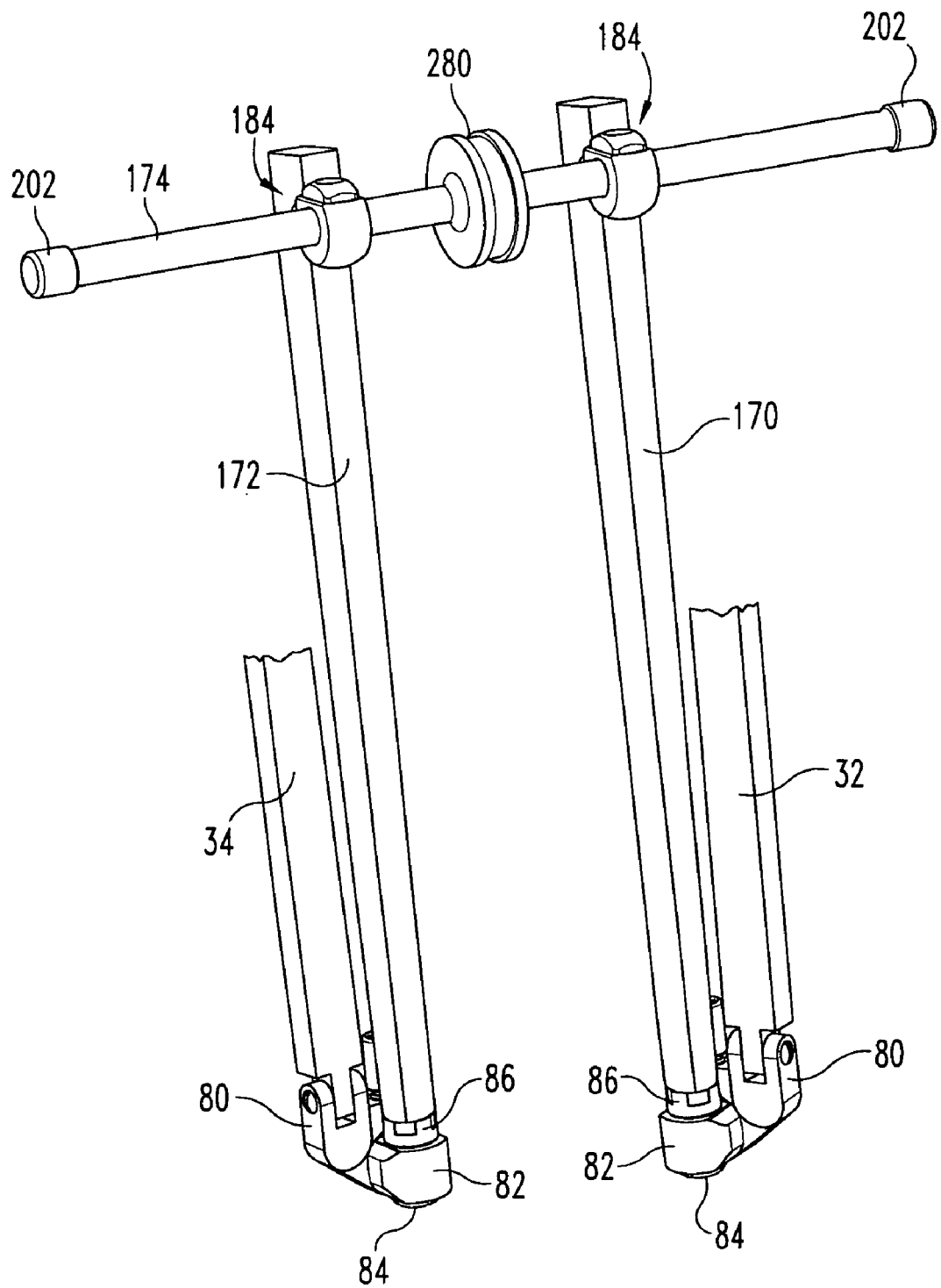
FIG. 17 is a perspective view of an embodiment of additional structure attached to the embodiment of FIG. 1, with only parts of the embodiment of FIG. 1 shown.
Figure 21:
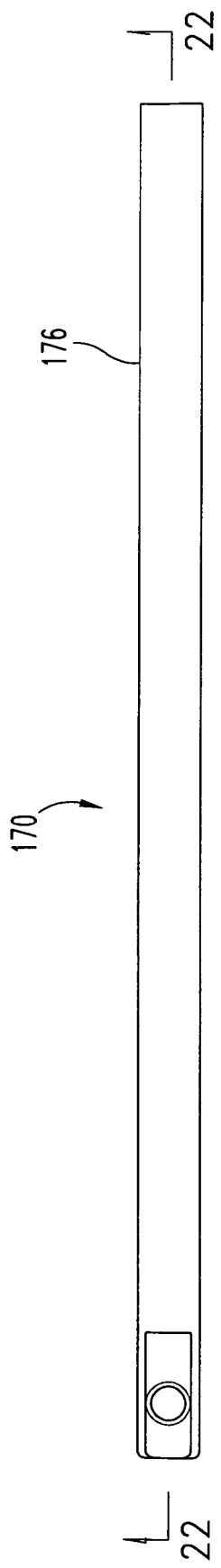
FIG. 21 is a side view of another aspect of the embodiment shown in FIG. 17.
Figure 22:
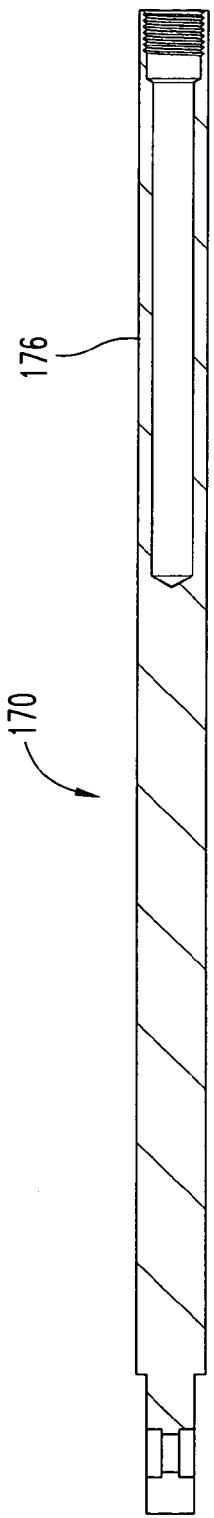
FIG. 22 is a cross-sectional view of the structure shown in FIG. 21, taken along the lines 22-22 in FIG. 21 and viewed in the direction of the arrows.
Figure 23:
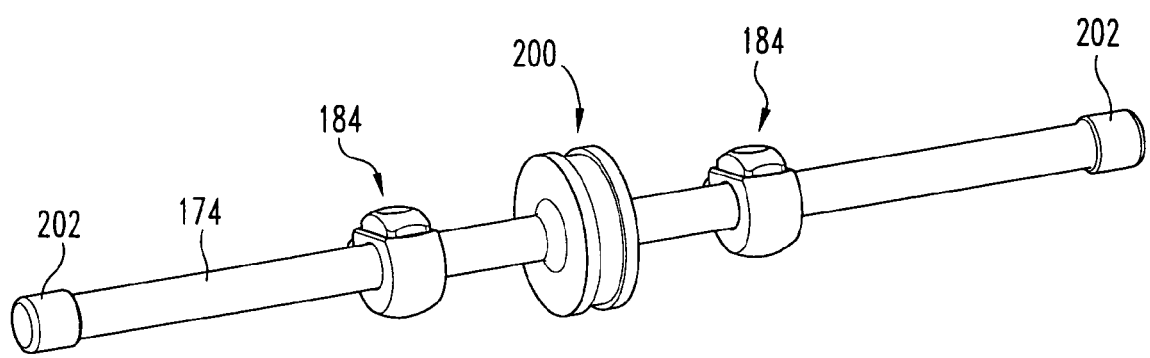
FIG. 23 is a perspective view of aspects of the embodiment shown in FIG. 17.
Figure 24:
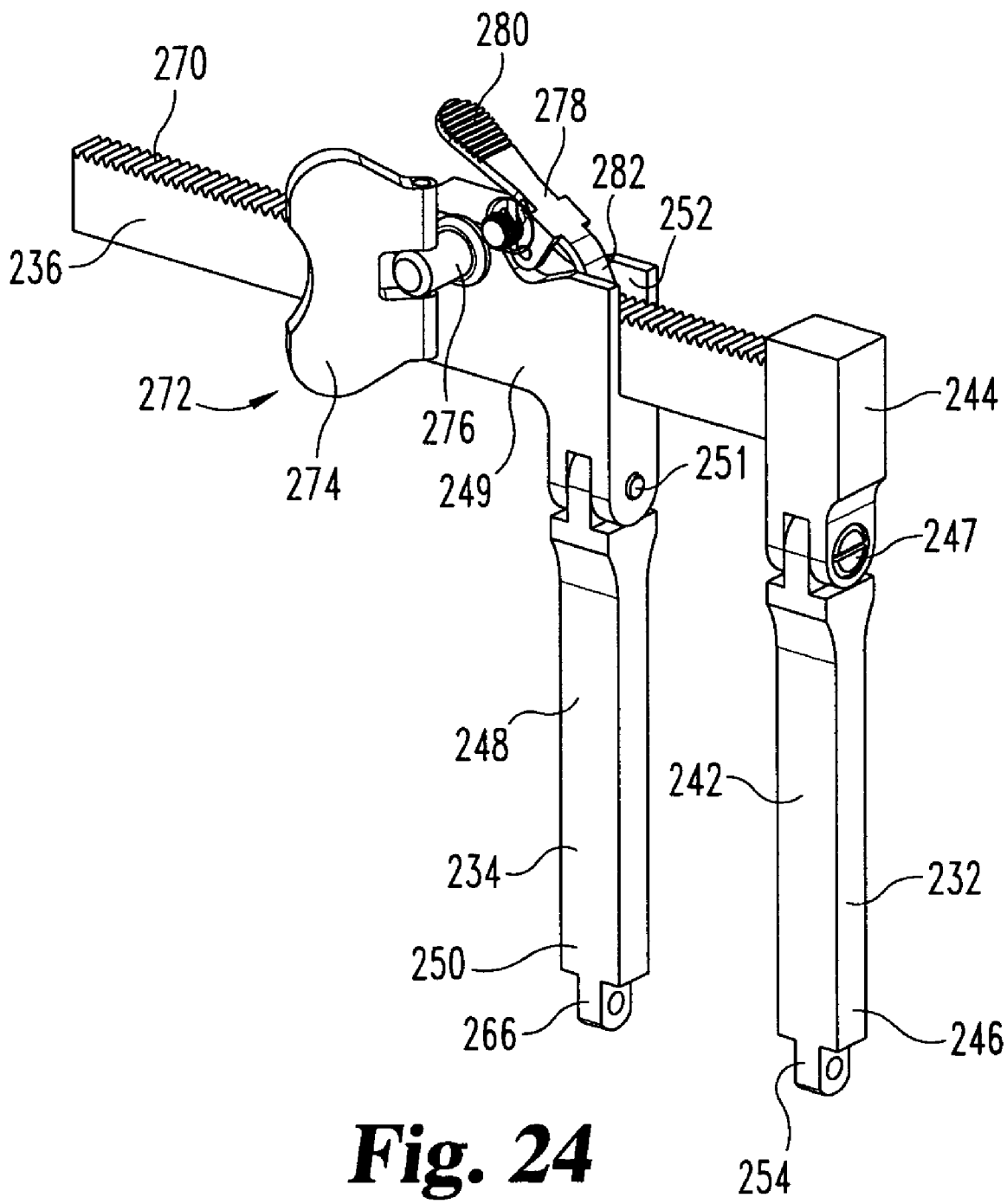
FIG. 24 is a perspective view of part of another embodiment of an instrument useful in orthopedic surgery.
Figure 25:
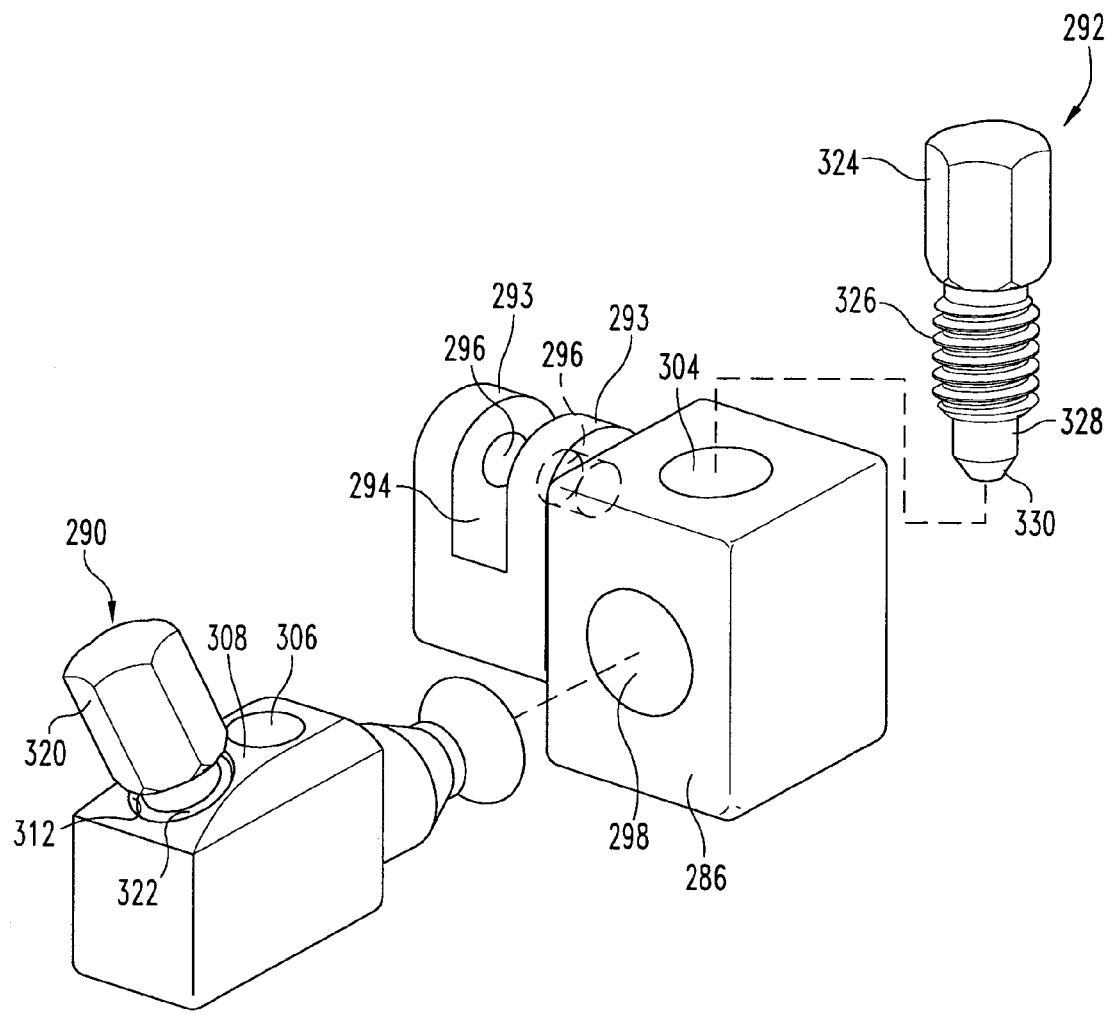
FIG. 25 is an exploded view in perspective of an assembly connectable with the embodiments shown in FIGS. 1 and 24.
Figure 26:
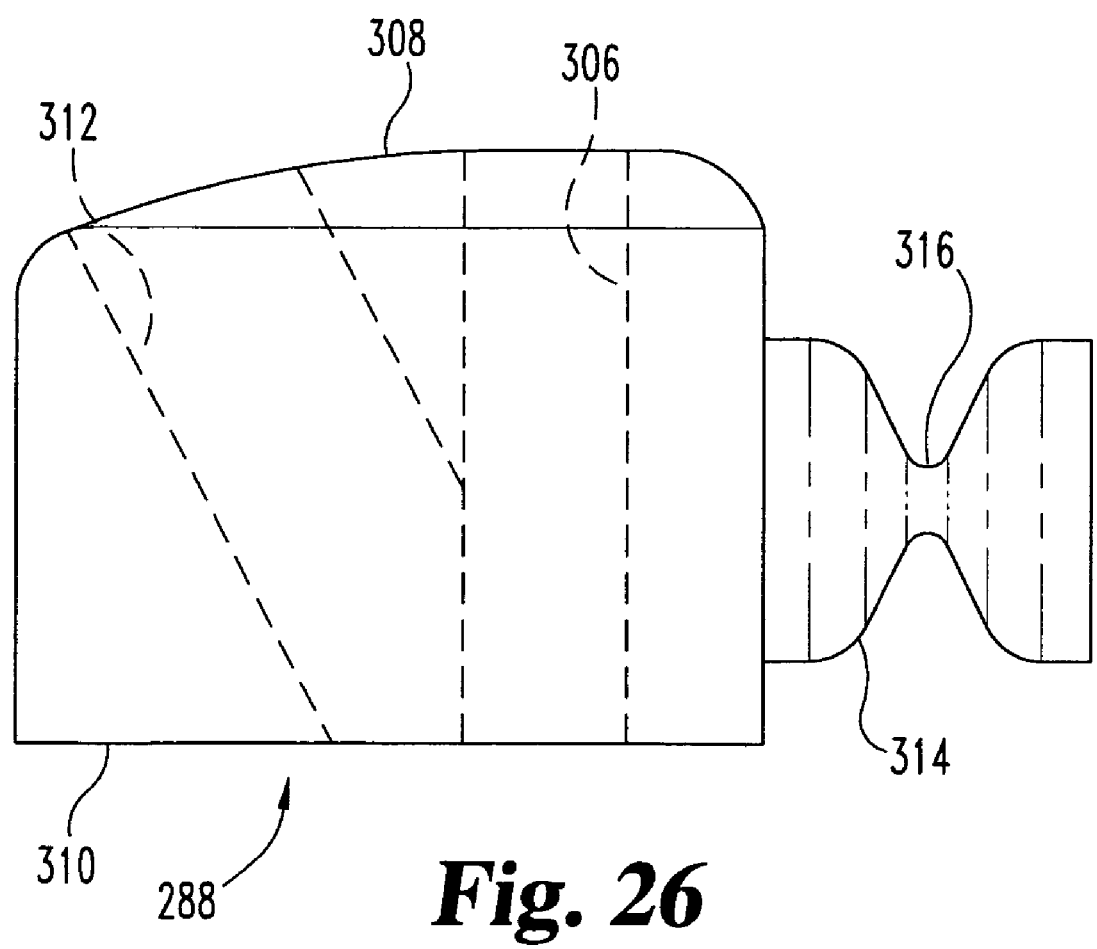
FIG. 26 is a side view of part of the structure shown in FIG. 25.

There may be provided with instrument 30 further structure to assist in angular adjustment of implants and their respective assemblies 38. Referring generally to FIG. 17 and related figures, two leverage arms 170 and 172 are connected by a threaded rod 174. Arms 170 and 172 are substantially identical, and therefore arm 170 will be further described below. Arm 170 may be at least partially hollow, having an opening in a lower end 176 that may be positioned over part of the associated assembly 38. The illustrated embodiment of opening 176 is substantially cylindrical with threads compatible with threads of collet 84. Opening 176 could be without threads, could include an internal print, for example a print sized and configured to accommodate nut 86, or could be otherwise configured.

An upper end 178 of arm 170 in the illustrated embodiment has a thin portion 180 with a hole 182. A grommet assembly 184 is connected to arm 170 via hole 182. Grommet assembly 184 includes a base 186 with a hole 188, an aperture 190 substantially transverse to hole 188, and a leg 189. A spring 192 is in aperture 190, and a button 194 with a threaded hole 196 sits in aperture 190 atop spring 192. Leg 189 may include an enlarged end 198 sized and configured to retain leg 189 in hole 182 of arm 170. In one particular embodiment, end 198 is attached to leg 189 after leg 189 is inserted through hole 182 and is fixed to leg 189, for example by gluing or welding. In other embodiments, end 198 can be flexible or elastically compressible, so that end 198 can be attached to or integral with leg 189, and can be forced through hole 182 without losing the ability to retain leg 189 in hole 182. Grommet assembly 184 can rotate with respect to arm 170 around an axis through leg 189 in the illustrated embodiment. The threads in hole 196 are compatible with threads on rod 174.

Rod 174 may have left-hand threads on one side, and right-hand threads on the other. In that case, one grommet assembly 184 will have left-hand threads and another grommet assembly 184 will have right-hand threads. Alternatively, rod 174 could have one type of thread on a threaded portion. A knob 200 may be provided for turning rod 174. In particular embodiments, knob 200 may be integrally formed with rod 174, or it may be made separately and attached to rod 174. Rod 174 may have flat portions compatible with gripping or turning tools. One or more end pieces 202 may be attached to rod 174 to retain one or more grommet assemblies 184 on rod 174.

In one embodiment, a grommet assembly 184 is connected to each of arms 170 and 172 before inserting rod 174 through such grommet assemblies 184. In that case, arms 170 and 172 can be used by themselves for leverage in applying rotational force to respective collets 84, nuts 86 and/or implants associated with them. Again referring singly to arm 170 for convenience, the illustrated embodiment of arm 170 may be connected to collet 84 by threading opening 176 of arm 170 onto threaded portion 130 of collet 84. In other embodiments, opening 176 may fit around, and possibly relatively closely with, nut 86 or an implant. Applying force to arm 170 causes rotation of extension 82 with respect to body 80 of assembly 38, and/or rotation of assembly 38 around axle 97 that connects body 80 and arm 32.

If desired, rod 174 can be connected to grommet assemblies 184 attached to arms 170, 172 by pressing buttons 194 and inserting rod 174 through holes 196 of buttons 194 and holes 188 of bases 186. Releasing buttons 194 engages threads of buttons 194 with threads of rod 174. In embodiments with left-hand and right-hand threads on rod 174 and grommet assemblies 184, turning knob 200 in one direction will force grommet assemblies 184 away from each other, turning arm 170 generally clockwise and arm 172 generally counterclockwise. Turning knob 200 in the other direction will force grommet assemblies 184 toward each other, turning arm 170 generally counterclockwise and arm 172 generally clockwise. In embodiments in which one type of thread (left-hand or right-hand) is on rod 174, turning knob 200 moves grommet assemblies 184 in the same direction, tending to move arms 170 and 172 through substantially the same angle. Knob 200 or a portion of rod 174 could be pushed or pulled so as to change the angulation of each assembly 38 by a similar or identical amount. Once the desired angles of the assembly 38 are achieved, they are tightened as indicated above to limit or inhibit further angular movement between extension 82 and connecting body 80. Arms 170 and 172 and the connecting rod 174 can then be slipped off assemblies 38 and removed from the surgical site. Compression or distraction, if not already performed and if desired, can be performed.

In an alternative embodiment, an instrument such as instrument 30 may have arms 232 and 234 connected by a toothed rod, bar or rack 236. Arm 232, in the illustrated embodiment, is substantially rectangular in cross-section along a medial portion 242, and has a first end 244 that connects to rod 236, and a second end 246. In the illustrated embodiment, end 244 is pivotably connected to medial portion 242 by an axle 247, which may be a screw or other threaded element. End 244 is fixed with respect to rod 236 in a particular embodiment, as by gluing, welding, interference fitting or otherwise. Arm 234 has a medial portion 248 connected to a first end 249 and a second end 250. The illustrated embodiment of end 249 is substantially L-shaped and is pivotably connected to medial portion 248 by an axle 251, which could be substantially identical to axle 247. End 249 has a channel 252 in which rod 236 sits, and is movable with respect to rod 236, as will be further discussed below. Each of arms 232 and 234 include a tongue 254, 266, substantially as described above with respect to tongues 50 and 66. Tongues 254, 266 may connect to an assembly such as assembly 38, or to an assembly 268 further described below, via an axle substantially as described above.

Rod 236 is shown in one embodiment as a flattened substantially rectangular solid. It will be understood that bar 236 could have any of a number of shapes, such as an elongated solid with a cross-section in the shape of a circle, square, triangle or other polygon. The illustrated embodiment of bar 236 includes a set of teeth or ridges 270 along one side, e.g. a top side.

In a specific embodiment a pinion mechanism 272 extends through a part of end 249 and into channel 252. Pinion mechanism 272, in one embodiment, has a handle 274 pivotably connected to a pinion 276, which has teeth or ridges in channel 252 and in contact with teeth 270 or rod 236 in rack-and-pinion fashion, so that turning pinion mechanism 272 results in linear movement of arm 234 with respect to rod 236. A locking pawl 278 may be included. In the illustrated embodiment, pawl 278 is a spring-loaded lever attached to end 249, having a pushing surface 280 and a tooth-engaging end 282. Pushing on pushing surface 280 rotates pawl 278 to disengage tooth-engaging end 282 from teeth 270 of rod 236, permitting free movement of arm 234 with respect to rod 236. Releasing pushing surface 280 allows tooth-engaging end 282 to resume its spring-biased position engaging teeth 270. In embodiments having rod 236, arms 232 and 234, and pinion mechanism 272 and pawl 278 if included, are pre-assembled prior to surgery to form essentially a single "rack" unit for the surgeon's use.

In the illustrated embodiment, pawl 278 is oriented to allow distraction while pawl 278 is in its spring-biased state (i.e. when tooth-engaging end 282 engages teeth 270), while limiting or preventing compression. To enable compression of vertebrae, pawl 278 may be disengaged from teeth 270 in the illustrated embodiment, or may be oriented 180 degrees opposite to what is shown in the illustrated embodiment, or may be left out altogether.

Assemblies 268 can clamp on to implants. In the illustrated embodiment, each of the assemblies 268 includes a connector body 286, an extension 288, a set screw 290, and a set screw 292. Connector body 286 is similar to connector body 80 described above, and includes two prongs 293 forming a slot 294. Substantially collinear holes 296 are formed in each prong 293, and accommodate a set screw or axle for connecting connector body 286 pivotably with tongue 254 of arm 232 (or tongue 266 of arm 234). Connector body 286 further includes a hole 298 into or entirely through connector body 286. Connector body 286 includes a threaded hole 304 for set screw 292.

The illustrated embodiment of extension 288 includes a hole 306 from a top surface 308 to a bottom surface 310. A threaded hole 312 is provided in extension 288 that communicates with hole 306, and into which set screw 290 may be threaded, as described further below. In one embodiment, hole 312 is at an oblique angle with respect to hole 306, and in other embodiments may form any of a variety of angles with respect to hole 306. Extension 288 further includes an extending leg 314 which includes a groove 316 that in the illustrated embodiment is substantially V-shaped. The surfaces of groove 316 may be relatively smooth, or may be roughened.

Set screw 290 includes a head portion 320 and a threaded portion 322. Threaded portion 322 may end in a conical surface that may be smooth or roughened, or may be threaded all the way to the end. As noted above, set screw 290 is threaded into hole 312 in extension 288. Set screw 290 is threaded into extension 288 far enough so that an end portion of threaded portion 322, or a thread of threaded portion 322, may contact a bone implant within hole 306 of extension 288.

An embodiment of set screw 292 has a head portion 324, a threaded portion 326, and a tapered tip 328. Head 324 and threaded portion 326 are substantially the same as those of set screw 290. Tapered tip 328 has a portion with a substantially constant diameter that is equal to or less than the root diameter of threaded portion 326. Below that substantially constant diameter area, there is a tapered portion 330 that may be substantially conical. Set screw 292 is threaded into threaded hole 304 in connector body 286, so that tapered tip 328 at least partially enters groove 316 of extension 288. Tightening set screw 292 against extension 288 substantially prevents or inhibits rotation of extension 288 with respect to connecting body 286 around a longitudinal axis through leg 314 of extension 288.

The description given above concerning surgical preparation, techniques, implantation and use of instrument 30 is equally applicable here. Implants fastened to bone tissue are inserted into holes 306 of the respective assemblies 268, and set screw 290 is tightened so that it contacts a portion of the implant and substantially prevents or inhibits the motion of the implant with respect to extension 288. The surgeon can rotate extension 288 with respect to connecting body 286 until he or she tightens set screw 292 sufficiently. When set screws 290 and 292 are tightened, fixing implants with respect to respective assemblies 268, distraction or compression can occur by operating pinion mechanism 272 to move arms 232 and 234 away from or toward each other. Once a satisfactory distraction or compression has been achieved, set screws 290 for each assembly 268 may be loosened, allowing assemblies 268 and the rest of the instrument to be pulled away from the bone implants and away from the surgical site.

It will be appreciated that the parts of the embodiments shown and described may be made of biocompatible materials such as stainless steel, titanium, ceramics or hard plastics, or other known or developed biocompatible materials. Materials that can be easily sterilized and reused may be particularly useful.

In the embodiments shown and described above, bodies 80, 280 are essentially flat, and extensions 82, 282 are located to the side of and below prongs 92, 292 and perpendicular to connecting bodies 80, 280. Other embodiments may find extension 82, 282 directly below, directly to the side, or otherwise situated with respect to prongs 92, 292. Yet other embodiments may have an angle in body 80, 280, so that leg portions 114, 314 of extension 82, 282 may be at an oblique angle to a line connecting prongs 92, 292, or may be parallel to such a line. Body 80, 280 may be constructed so that extension 82 is a relatively substantial distance ahead, behind, or to the side of prongs 92, 292. It is further noted that extension 82 has a substantially rounded shape, while extension 282 is substantially rectangular. Other shapes of extensions 82, 282, and alternative shapes of portions of connecting body 20, may be used in other embodiments. Assemblies 38 and 268 may be modified by adding or replacing parts with parts from another embodiment, e.g. splines or locking set screws. Assemblies 38 and 268 may be used with a variety of arms and/or structure connecting such arms, including those disclosed above.

Rod 36, in alternative embodiments, may be roughened or smooth rather than threaded. In such embodiments, alternative mechanisms for controlling arm 34, including moving arm 34 relative to arm 32, can be provided. Further, in other embodiments it may be arm 34 that is fixed and arm 32 that is movable with respect to rod 36.

While the illustrated embodiments show two arms each with an assembly as disclosed, it will be seen that an instrument can be made and used in which one such arm (e.g. arm 32) is provided with an assembly such as assembly 38 or 268, and a different structure or mechanism is provided for connecting to a bone, implant or other object.

The U.S. patent application Ser. No. 11/118,513, entitled ORTHOPEDIC INSTRUMENT, filed on Apr. 29, 2005, first-named inventor Bryan S. Wilcox, is incorporated herein by reference in its entirety.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An apparatus for connecting to at least one orthopedic implant, comprising:
   an arm;
   an elongated member connected to said arm, said arm being movable along the length of said elongated member;
   an assembly connected to said arm, said assembly including a connecting body connected to said arm so that said connecting body can pivot with respect to said arm, an extension connected to said connecting body so that said extension can pivot with respect to said connecting body, and a locking member connected to said connecting body and having a loosened state wherein said extension can pivot with respect to said connecting body, and a tightened state wherein said extension is locked with respect to said connecting body,
   wherein said connecting body has an opening, and said extension has a hole in which an implant may be placed and locked and a leg portion that extends into said opening in said connecting body,
   wherein said locking member includes a screw and a block connected to said screw, said block contacting said leg of said extension when said locking member is tightened, and
   wherein said leg of said extension includes splines, said block contacting said splines when said locking member is tightened.

2. The apparatus of claim 1, wherein said opening of said connecting body has a surface with splines, and said splines of said leg of said extension engage said splines of said connecting body when said locking member is tightened.

3. The apparatus of claim 1 further comprising a collet inserted in said hole of said extension, said collet being hollow so that an implant can be inserted in said collet, said collet having one or more slots making a portion of said collet compressible around the implant.

4. The apparatus of claim 1 wherein said extension has a second hole that communicates with said implant hole for accommodating a screw, and further comprising a screw insertable into said screw hole for locking said implant with respect to said extension.

5. The apparatus of claim 1 wherein said elongated member is at least partially threaded.

6. The apparatus of claim 5 wherein said arm has a threaded portion compatible with the threads of said elongated member.

7. The apparatus of claim 6 further comprising a button and a spring connected to said arm, said button having a hole therethrough that includes said threaded portion of said arm, so that in a spring-biased state said threaded portion of said hole of said button engages said threaded portion of said elongated member, and pressing said button against said spring disengages said threads.

8. The apparatus of claim 1, wherein said connecting body includes a pair of prongs defining a slot, each said prong having a hole therethrough, and said arm includes a tongue with a hole, said tongue fitting in said slot so that said hole of said tongue is substantially collinear with said holes in said prongs, and further comprising an axle extending through said holes in said prongs and said hole in said tongue, so that said connecting body can be pivoted about said axle with respect to said arm.

9. The apparatus of claim 8, wherein at least one of said holes in said prongs is at least partially threaded, and said axle is a screw.

10. The apparatus of claim 1, further comprising a second arm connected to said elongated member, said second arm being substantially immovable along said elongated member.

11. The apparatus of claim 10, further comprising an assembly connected to said second arm, said assembly including a connecting body connected to said second arm so that said connecting body can pivot with respect to said second arm, an extension connected to said connecting body so that said extension can pivot with respect to said connecting body, and a locking member connected to said connecting member and having a loosened state wherein said extension can pivot with respect to said connecting body, and a tightened state wherein said extension is locked with respect to said connecting body.

12. The apparatus of claim 11, wherein said elongated member is at least partially threaded, and said movable arm has a threaded portion compatible with the threads of said elongated member, and said second arm allows rotation of said elongated member with respect to it without substantial movement of said second arm along said elongated member.

13. The apparatus of claim 11, further comprising a rotational adjusting mechanism, said mechanism including
    a first leverage arm connected to a part of said assembly associated with said movable arm or an implant in that assembly,
    a second leverage arm connected to a part of said assembly associated with said second arm or an implant in that assembly,
    a first grommet assembly connected to said first leverage arm, said first grommet assembly having a threaded portion and a release mechanism;
    a second grommet assembly connected to said second leverage arm, said second grommet assembly having a threaded portion and a release mechanism; and
    an elongated member that is at least partially threaded inserted into said first and second grommet assemblies so that a threaded portion of said elongated member is adjacent said threaded portions of said grommet assemblies.

14. The apparatus of claim 13, further comprising a knob connected to said elongated member.

15. The apparatus of claim 14, wherein operating one of said release mechanism disengages said threaded portion of the respective grommet assembly from said elongated member.

16. The apparatus of claim 1, wherein said elongated member has teeth, and further comprising a pinion connected to said teeth and to said arm, whereby turning said pinion moves said arm with respect to said elongated member.

17. An apparatus for connecting to at least one orthopedic implant, comprising:
    an arm;
    an elongated member connected to said arm, said arm being movable along the length of said elongated member;
    an assembly connected to said arm, said assembly including a connecting body connected to said arm so that said connecting body can pivot with respect to said arm, an extension connected to said connecting body so that said extension can pivot with respect to said connecting body, and a locking member connected to said connecting body and having a loosened state wherein said extension can pivot with respect to said connecting body, and a tightened state wherein said extension is locked with respect to said connecting body; and
    a collet inserted into said extension and having a threaded portion, and a nut threadable on said threaded portion of said collet, wherein tightening said nut on said collet against a surface of said extension draws said collet along said extension.

18. The apparatus of claim 17, wherein said locking member includes a screw.

19. The apparatus of claim 18, wherein said locking member includes a block connected to said screw, said block contacting said extension when said locking member is tightened.

20. The apparatus of claim 18, wherein said screw includes a tapered tip that contacts said extension when said locking member is tightened.

21. The apparatus of claim 20, wherein said extension includes a groove, and said tapered tip contacts a surface of said groove when said locking member is tightened.

22. The apparatus of claim 17, wherein said collet has one or more slots making a portion of said collet compressible around the implant.

23. The apparatus of claim 22, wherein said collet includes a compressible portion, said compressible portion of said collet has a convex exterior, and said compressible portion of said collet has an outer diameter in an uncompressed state that is at least slightly larger than an inner diameter of a hole of said extension that receives said collet.

24. The apparatus of claim 17 wherein said elongated member is at least partially threaded.

25. The apparatus of claim 24 wherein said arm has a threaded portion compatible with the threads of said elongated member.

26. The apparatus of claim 25 further comprising a button and a spring connected to said arm, said button having a hole therethrough that includes said threaded portion of said arm, so that in a spring-biased state said threaded portion of said hole of said button engages said threaded portion of said elongated member, and pressing said button against said spring disengages said threads.

27. The apparatus of claim 17, wherein said connecting body includes a pair of prongs defining a slot, each said prong having a hole therethrough, and said arm includes a tongue with a hole, said tongue fitting in said slot so that said hole of said tongue is substantially collinear with said holes in said prongs, and further comprising an axle extending through said holes in said prongs and said hole in said tongue, so that said connecting body can be pivoted about said axle with respect to said arm.

28. The apparatus of claim 27, wherein at least one of said holes in said prongs is at least partially threaded, and said axle is a screw.

29. The apparatus of claim 17, further comprising a second arm connected to said elongated member, said second arm being substantially immovable along said elongated member.

30. The apparatus of claim 29, further comprising an assembly connected to said second arm, said assembly including a connecting body connected to said second arm so that said connecting body can pivot with respect to said second arm, an extension connected to said connecting body so that said extension can pivot with respect to said connecting body, and a locking member connected to said connecting member and having a loosened state wherein said extension can pivot with respect to said connecting body, and a tightened state wherein said extension is locked with respect to said connecting body.

31. The apparatus of claim 30, wherein said elongated member is at least partially threaded, and said movable arm has a threaded portion compatible with the threads of said elongated member, and said second arm allows rotation of said elongated member with respect to it without substantial movement of said second arm along said elongated member.

32. The apparatus of claim 17, wherein said elongated member has teeth, and further comprising a pinion connected to said teeth and to said arm, whereby turning said pinion moves said arm with respect to said elongated member.

33. An apparatus for connecting to at least one orthopedic implant, comprising:
a first arm;
a first elongated member connected to said first arm, said first arm being movable along the length of said first elongated member;
a second arm connected to said first elongated member, said second arm being substantially immovable along said first elongated member;
wherein said first elongated member is at least partially threaded, and said first arm has a threaded portion compatible with the threads of said first elongated member, and said second arm allows rotation of said first elongated member with respect thereto without substantial movement of said second arm along said first elongated member;
a first assembly connected to said first arm, said first assembly including a first connecting body connected to said first arm so that said first connecting body can pivot with respect to said first arm, a first extension connected to said first connecting body so that said first extension can pivot with respect to said first connecting body, and a first locking member connected to said first connecting body and having a loosened state wherein said first extension can pivot with respect to said first connecting body, and a tightened state wherein said first extension is locked with respect to said first connecting body;
a second assembly connected to said second arm, said second assembly including a second connecting body connected to said second arm so that said second connecting body can pivot with respect to said second arm, a second extension connected to said second connecting body so that said second extension can pivot with respect to said second connecting body, and a second locking member connected to said second connecting member and having a loosened state wherein said second extension can pivot with respect to said second connecting body, and a tightened state wherein said second extension is locked with respect to said second connecting body;
a collet inserted into each of said first and second extensions and having a threaded portion, and a nut threadable on said threaded portion of said collet, wherein tightening said nut on said collet against a surface of a respective one of said extensions draws said collet along said respective one of said extensions;
a rotational adjusting mechanism, said mechanism including
a first leverage arm connected to a part of said first assembly associated with said movable first arm or an implant in said first assembly,
a second leverage arm connected to a part of said second assembly associated with said second arm or an implant in said second assembly,
a first grommet assembly connected to said first leverage arm, said first grommet assembly having a first threaded portion and a first release mechanism;
a second grommet assembly connected to said second leverage arm, said second grommet assembly having a second threaded portion and a second release mechanism; and
second elongated member that is at least partially threaded inserted into said first and second grommet assemblies so that a threaded portion of said second elongated member is adjacent said first and second threaded portions of said first and second grommet assemblies.

34. The apparatus of claim 33, further comprising a knob connected to said second elongated member.

35. The apparatus of claim 34, wherein operating one of said first and second release mechanisms disengages said threaded portion of the respective grommet assembly from said second elongated member.

* * * * *

UNITED STATES PATENT AND TRADEMARK OFFICE
CERTIFICATE OF CORRECTION

PATENT NO. : 7,578,822 B2
APPLICATION NO. : 11/118641
DATED : August 25, 2009
INVENTOR(S) : Rezach et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 991 days.

Signed and Sealed this

Seventh Day of September, 2010

David J. Kappos
*Director of the United States Patent and Trademark Office*